US00PP14750P3

(12) United States Plant Patent
Orton et al.

(10) Patent No.: US PP14,750 P3
(45) Date of Patent: May 4, 2004

(54) ILEX INTERSPECIFIC HYBRID NAMED 'RUTZAN'

(50) Latin Name: *Ilex (×meserveae)×I. pernyi*
Varietal Denomination: Rutzan

(75) Inventors: Elwin R. Orton, Millstone, NJ (US); David A. Gant, Wall Township, NJ (US)

(73) Assignee: Rutgers, The State University, New Brunswick, NJ (US)

( * ) Notice: Subject to any disclaimer, the term of this patent is extended or adjusted under 35 U.S.C. 154(b) by 41 days.

(21) Appl. No.: 10/195,001

(22) Filed: Jul. 11, 2002

(65) Prior Publication Data

US 2004/0010828 P1 Jan. 15, 2004

(51) Int. Cl.[7] ..... A01H 5/00

(52) U.S. Cl. ..... Plt./247

(58) Field of Search ..... Plt./247

*Primary Examiner*—Kent Bell
(74) *Attorney, Agent, or Firm*—James A. Lucas

(57) ABSTRACT

Rutzan is a new and distinct variety of evergreen holly distinguished in that it combines from three species (*Ilex aquifolium, Ilex rugosa,* and *Ilex pernyi*), desirable landscape and production traits which distinguish it from all other forms of Ilex. Plants of the new variety exhibit a moderate rate of growth, develop a densely branched narrow to moderately broad conical form of compact size, possess small to medium sized dark green spiny leaves, produce an abundance of bright red fruit well displayed on wood of the previous season's growth, and are outstanding for their exceptionally high level of winter hardiness.

2 Drawing Sheets

Figure 1:
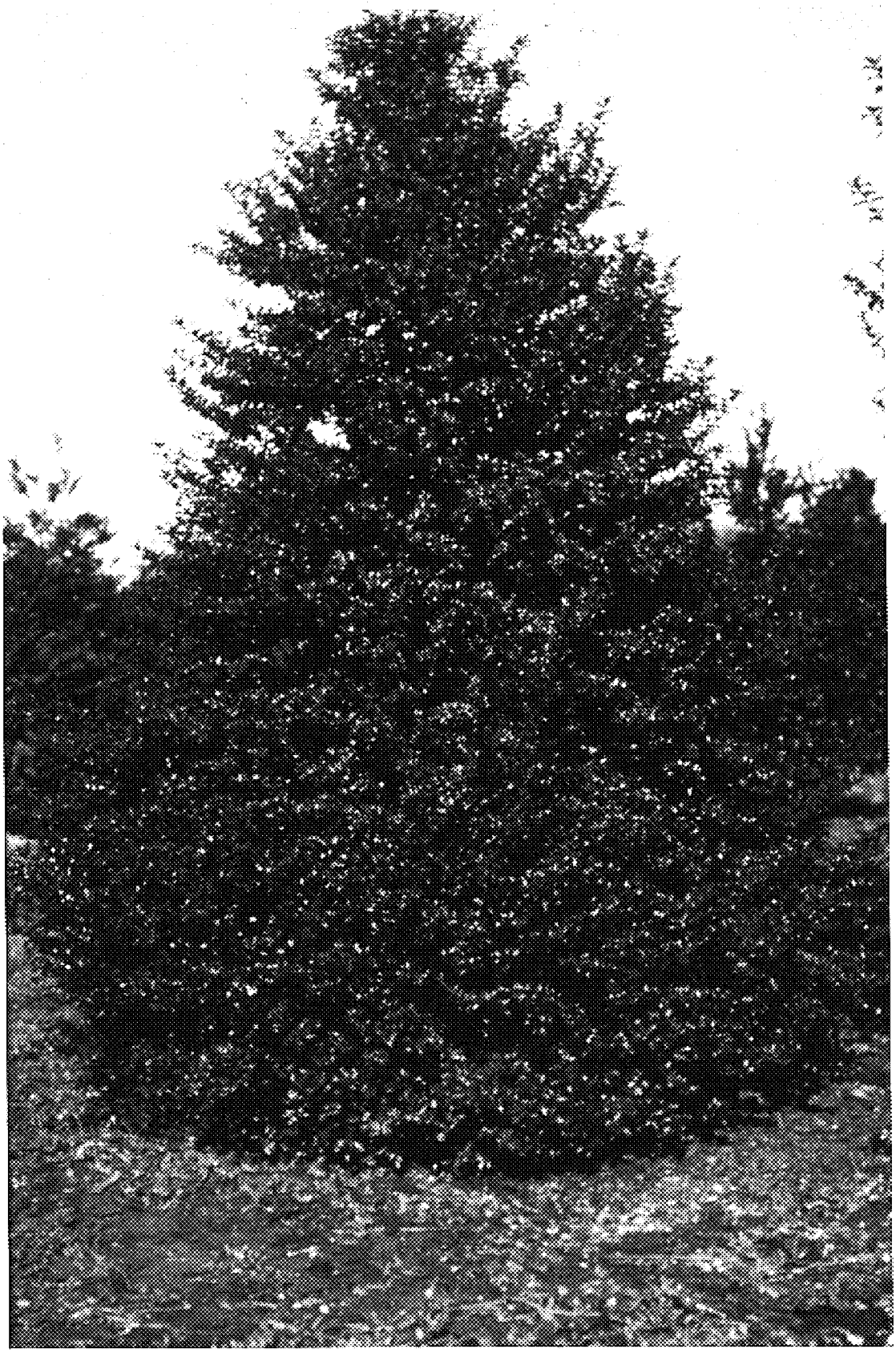

Latin name of genus and species: *Ilex* (×*meserveae*)×*I. pernyi.*
Variety name: Rutzan.

BACKGROUND OF THE PRESENT INVENTION

Our breeding objective was to create an evergreen holly tree which embodies our ideas of desirability and other characteristics which would make the same commercially attractive and thereby having high potential for commercial distribution, and we believe we have been successful in achieving that goal. Other important selection factors may include ultimate plant size and shape, disease resistance, tolerance to different soil and growing conditions and vigor.

To our knowledge, plants of these three species combination have not been reported previously. The new clone has been named the 'Rutzan' variety.

BRIEF SUMMARY OF THE INVENTION

Our invention is a novel, unique, and highly ornamental form of Ilex which was originated by us by crossing an unnamed and unpatented $F_2$ generation pistillate seedling of *Ilex×meserveae* (*Ilex rugosa×Ilex aquifolium*) with an unnamed and unpatented staminate seedling of the species known botanically as *Ilex pernyi.*

The variety exhibits the following combination of traits:

(a) a moderately vigorous, dense and self-compacting evergreen tree of a narrow to moderately broad conical form of much less height and size than that of most tree forms of *Ilex aquifolium* known to us, (b) evergreen leaves which are primarily ovate with a truncate base, spinose margin, slightly reflexed acuminate tip, and which are dark green and shiny, (c) an abundance of pistillate flowers well positioned on shoots of the previous year's growth and providing a well distributed and very showy set of fruit maturing to a bright red in the early fall and then persisting throughout the winter, (d) winter hardiness that we believe to be superior to that of all varieties of *I. aquifolium* and *I. pernyi,* and heat tolerance superior to that to all varieties of *Ilex Aquifolium* and *Ilex rugosa* known to us, and (e) low susceptibility to disease and insect pests.

In a production environment, plants of Rutzan variety develop a dense, self-compacting, conical growth habit with strong apical dominance without corrective pruning, and their small size relative to the larger tree form typical of plants of *Ilex aquifolium,* or hybrids of *Ilex aquifolium×Ilex pernyi,* makes them useful in a wider range of landscape settings.

BRIEF DESCRIPTIONS OF THE DRAWINGS

The color definitions in the specification have been taken from The R.H.S. Colour Chart of The Royal Horticultural Society, London, England. The colors depicted are believed to be of a high level of color fidelity and are believed to be as close to the actual coloration of the plant as possible in a photographic illustration of this quality. However, due to factors such as light reflectance, cultural conditions and horticultural practices, the coloration of this plant should be understood to be approximate. For example, the leaf color may vary depending on the composition and the concentration of fertilizer that may be applied to the plant.

Figure 2:
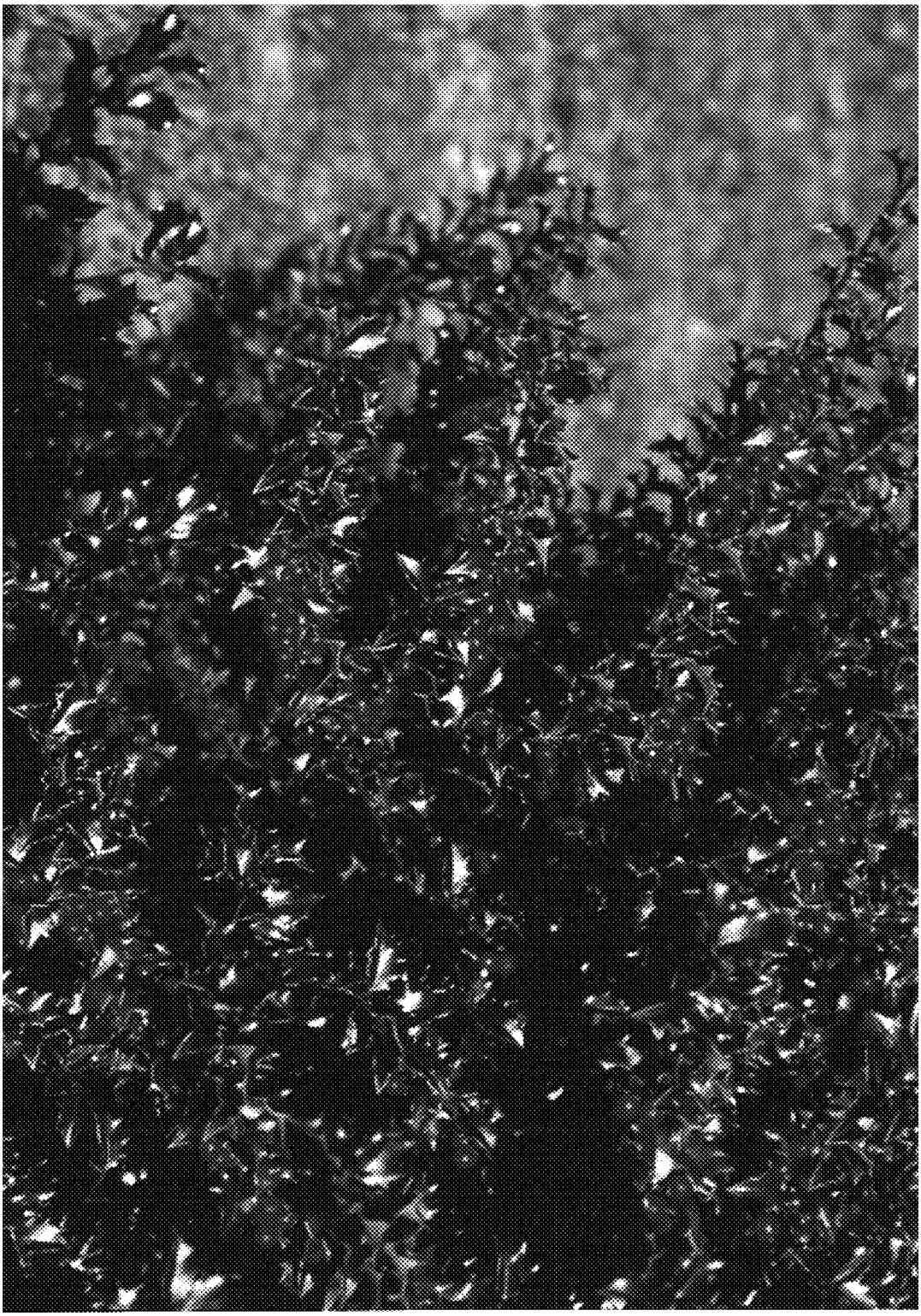

FIG. 1 illustrates the natural unpruned growth habit and foliage and fruit characteristics of a nine year cutting-grown plant of the new variety, and FIG. 2 illustrates typical foliage and fruit of the new variety.

BOTANICAL DESCRIPTION OF THE PLANT

The following is a detailed description of our new variety of Ilex made from observation of the original seedling growing in the ground in the vicinity of New Brunswick, N.J. and of nine-year-old plants growing in the ground at Adelphia, N.J.

Parentage: $F_2$ generation pistillate seedling of (*Ilex*× *meserveae*)×*Ilex pernyi.*

*Pollinator.*—Plant may be pollinated by a staminate plant of either *Ilex aquifolium, Ilex pernyi, Ilex rugosa, Ilex*×*aquipernyi,* or *Ilex*×*meserveae* with synchronous flowering period.

Plant growth characteristics: Plants have an upright, rather narrow conical habit with nine-year field-grown plants attaining a size of 1.75 to 2.5 m in height and 1.5 m in width under conditions of minimal fertilization and minimal supplemental irrigation. Plants establish a dominant central trunk and branching is dense and self-compacting with very little or no pruning. Diameter of the tree trunk at 10 cms above the soil level is typically 3.5 to 4.1 cms. The bark texture of the trunk is smooth and Greyed-Green Group 197C, becoming Yellow-Green Group 146B with stripes of Greyed-Green Group 197C higher on the trunk. Plants bear annual abundant crops of beautiful red berries which are attractively displayed among the semi-glossy dark green, spiny leaves which do not become lighter green when bearing a heavy crop of fruit as do the leaves of many varieties of Ilex.

A plant in the mature phase (flowering) can be achieved in one year from a rooted cutting taken from a plant in the mature phase and the subsequent annual growth rate ranges from 20–30 cms for plants grown in full sun, varying as indicated depending on climatic conditions and soil type or type of artificial growing medium utilized and cultural practices such as fertilization and irrigation.

Foliage:

*Type.*—Evergreen, coriaceous, semi-glossy. Leaves primarily ovate oblong with a truncate base, spinose margin, reflexed acuminate apex with a prominent terminal spine. Leaves borne alternatively along stem at a density of one leaf per 7.0 mm length of stem.

*Size.*—Leaf size varies with light intensity and fertility program where plants are growing. Size is generally in the range of 3–4.5 cm long and 2.0–2.6 cm wide.

*Petiole.*—Approximately 3–4 mm long and 1–2 mm wide, color is Yellow-Green Group 146C.

*Color.*—Mature levels, upper surface — closest to but slightly greener than Green Group 139A; under surface — Yellow-Green Group 146C. Leaves are semi-glossy.

Stems:

*Color.*—Tip 2.5–3 cm of new spring growth is Yellow-Green Group 144A and basal area is Yellow-Green Group 146B with fine stripes of a slight reddish tinge (177E Greyed-Orange Group). One year old stems are Yellow-Green Group 146B; older branches and the central stem are Yellow-Green Group 146B with stripes of Greyed-Green Group 197C, and base of the tree trunk is Greyed-Green Group 197C.

Numerous, dense, horizontal branches. Current season's new growth 2.0–2.5 mm in diameter. One year old branch 8.0 to 12.0 cms in length and 3.0–4.0 mm in diameter. Older wood progressively larger in diameter.

Inflorescence and fruit:

*Flowers.*—Small on pedicels 2 to 4 mm long borne on 1 mm spurs in leaf axils of previous year's growth, depth — 4.9 mm, diameter — 6 mm, fragrance — none detected, lastingness of bloom approximately 6–8 days if pollination and fertilization occurs as soon as flower opens, otherwise 10–12 days depending on climatic factors such as rain, air temperature, sunlight and wind; regular calyx, corolla rotate, sepals 4–5 with a shape of an equilateral triangle, all three sides being 1 mm in length with the apex of the pyramid appearing very slightly rounded under magnification, margins being entire; petals 4–5; petal basically oval with a length averaging 3.6 mm, width averaging 2.8 mm, base truncate, margin entire, apex rounded; buds form during August and September in the axils of the leaves and appear as tiny nodules of tissues. In following growing season, buds continue to develop and take on a specific observable form which changes continuously in shape, length and diameter until completely developed and about to open; Just prior to unfolding of the petals which enclose the other floral parts, the abaxial surface of the petals is 155A White Group with a hint of 145C Yellow-Green Group with a tiny rather circular area of 46A Red Group which extends as a central minute stripe halfway toward the petal base. The adaxial surface of the petals of an open flower is also 155A White Group with a hint of 145C Yellow-Green Group. It should be noted that there is nothing about the flowers and sepals of this variety that serves to distinguish it over other hollies.

Fruit:

*Type.*—Drupe containing 4, occasionally 5, woody pyrenes.

*Size.*—Rounded, approximately 0.95 cm, with a black, 4–5 lobed stigmatic scar.

*Color.*—At maturity fruit are semi-glossy, Red Group 45A.

Excluding the apical two or three leaves on the growth of the previous seasons, the fruit borne singly on pedicels in the axil of each lower leaf average 5.18 fruit borne at the axil of each leaf.

Reproductive organ:

*Pistil.*—1; — Stigma1; stigma is sessile on the ovary, therefore, there is no style; Ovary — 1 with 4, occasionally 5 loculi. Stamens — 4 and occasionally 5, pollen not produced as plant is a pistillate, filaments and anthers that comprise the stamens are not fully developed.

*Pedicel.*—Length 2.0 mm; width — 3 mm; color — 144C Yellow-Green Group; ovary height 3.1 mm; width 2.3 mm; color, 144C Yellow-Green Group; Stigma — 1 mm; 4 and occasionally 5 lobed, color — 144B Yellow-Green Group; on mature fruit color is 187A Greyed-Purple Group; Filament — length — 4.0 mm; width 0.5 mm; color 155 D White Group; Anther — length — 1.0 mm; width — 0.75 mm; color 155D White Group, 2 loculi.

Environmental tolerance: Field grown plants of this new variety exhibit winter hardiness in U.S.D.A. Plant Hardiness Map (January 1990) Zone 6a (−10° F.) superior to most, if not all, hybrid varieties of hollies of erect, single-trunked tree habit that involve *Ilex aquifolium* and/or *Ilex pernyi* as a parent known to us. No insect or disease damage has been observed on plants growing in the field. Asexual reproduction by cuttings and grafts of our new variety has been accomplished in the vicinity of New Brunswick, N.J. The plant reproduces true to type in successive generations of asexual reproduction.

What we claim is:

1. A new and distinct interspecific hybrid variety of Ilex plant named 'Rutzan' substantially as herein shown and described.

* * * * *